United States Patent
Schlangen et al.

(10) Patent No.: US 8,378,574 B2
(45) Date of Patent: Feb. 19, 2013

(54) LIGHTING SYSTEM FOR CREATING A BIOLOGICAL EFFECT

(75) Inventors: Lucas Josef Maria Schlangen, Eindhoven (NL); Gregorius Wilhelmus Maria Kok, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 612 days.

(21) Appl. No.: 12/600,702

(22) PCT Filed: May 23, 2008

(86) PCT No.: PCT/IB2008/052039
§ 371 (c)(1),
(2), (4) Date: Nov. 18, 2009

(87) PCT Pub. No.: WO2008/146220
PCT Pub. Date: Dec. 4, 2008

(65) Prior Publication Data
US 2010/0171441 A1 Jul. 8, 2010

(30) Foreign Application Priority Data
May 25, 2007 (EP) .................................... 07108905

(51) Int. Cl.
*H01J 7/24* (2006.01)
(52) U.S. Cl. ............. 315/50; 315/51; 315/313; 313/485
(58) Field of Classification Search .................. 315/50, 315/51, 35, 294, 152, 312, 313; 313/485, 313/487; 362/231; 345/102
See application file for complete search history.

(56) References Cited

U.S. PATENT DOCUMENTS

| | | | | |
|---|---|---|---|---|
| 2007/0145915 A1* | 6/2007 | Roberge et al. | ............... | 315/312 |
| 2007/0268234 A1* | 11/2007 | Wakabayashi et al. | ........ | 345/102 |
| 2009/0281604 A1* | 11/2009 | De Boer et al. | ................ | 607/88 |
| 2010/0060195 A1* | 3/2010 | Tsuboi et al. | ................. | 315/294 |
| 2010/0277316 A1* | 11/2010 | Schlangen et al. | ............ | 340/540 |

FOREIGN PATENT DOCUMENTS

| | | |
|---|---|---|
| EP | 0851462 A2 | 7/1996 |
| EP | 0915363 A2 | 5/1999 |
| EP | 1619648 A1 | 1/2006 |
| JP | 07282778 A | 10/1995 |
| WO | 0220079 A1 | 3/2002 |
| WO | 02052902 A2 | 7/2002 |

* cited by examiner

*Primary Examiner* — Vibol Tan
(74) *Attorney, Agent, or Firm* — John F. Salazar; Mark L. Beloborodov

(57) ABSTRACT

A lighting system for creating a biological effect induced by light. The biological effect is a different effect than vision. The lighting system comprises a light source (1) to generate light with a varying spectrum, and a driver (2) to drive the light source (1) to successively in time: (i) generate a first spectrum (S1) during a first period in time (T1), (ii) change the first spectrum (S1) into a second spectrum (S2) during a second period in time (T2), wherein the second spectrum (S2) has the biological effect, and (iii) maintain the second spectrum (S2) during a third period in time (T3). The duration of the second period in time (T2) is selected in a range from 5 seconds to 30 minutes. The first spectrum (S1) may not have the biological effect or may have the biological effect to a smaller extent than the second spectrum (S2).

9 Claims, 1 Drawing Sheet

LIGHTING SYSTEM FOR CREATING A BIOLOGICAL EFFECT

FIELD OF THE INVENTION

The invention relates to a lighting system, a consumer apparatus comprising the lighting system, and a method of driving a light source. The invention may be advantageously used for regulating the human circadian system.

BACKGROUND OF THE INVENTION

Light impacts human consciousness through the stimulation of the visual system. The human eye comprises, besides the receptors for seeing, another receptor located in the retina which is based on the photopigment melanopsin. The sensory system which comprises these receptors has, for humans, a peak wavelength sensitivity for the blue portion of the visible spectrum. The light impinging on these receptors regulates the circadian system of humans and other mammals.

WO02/20079 discloses a method of controlling the alertness of a human subject and a light source for use in this method. The method comprises exposure of the human subject to suitable light radiation during an exposure period, without substantially influencing the phase of a melatonin cycle. The suitable light radiation is specified by an output fraction of melatonin suppressive radiation and light output. The method may involve a shift from melatonin non-suppressive to suppressive radiation, depending on the time of the day, and is usable in applications to re-synchronize the biological clock in the case of multi-time-zone travel. The method is effectively used when the human subject is subjected to an overall exposure time of 30 minutes during which exposure periods alternate with (dark) interval periods, wherein the lamp is out of operation, of about 30 minutes. This prior art discloses the effect of suitable light radiation on melatonin suppression. However, the proposed approach does not have an optimal effect.

SUMMARY OF THE INVENTION

It is an object of the invention to provide a lighting system of which the light emitted has an improved biological effect other than vision.

In one aspect, the invention relates to a lighting system which includes: a light source generating light with a varying spectrum, and a driver for driving the light source. Advantageous embodiments are defined in the dependent claims.

Light sources which generate light with a varying spectrum are known. For example, WO02/052902 discloses a LED luminary with an array of red, green and blue LEDs. The color of the light emitted by the luminary can be varied by controlling the currents through the differently colored LEDs. EP0851462 discloses a lamp assembly which comprises two lamps producing light with different color temperatures. JP7282778 discloses a single fluorescent lamp which is able to change the quantity of blue light emission to red light emission by adjusting a duty ratio of a drive pulse. However, alternatively, any other lamp or lamp assembly of which the color is suitably adjustable may be used.

The driver drives the light source such that, successively in time, the following three states occur in the order mentioned. Firstly, a first spectrum is generated during a first period in time which has a first biological effect, or no biological effect at all. It has to be noted that, in the following, by biological effect is meant effects of the light other than vision. Examples of non-visual biological effects of light are: phase shifting using photic entrainment, inducing alertness (reaction times, vigilance, EEG activity), reducing sleep or fatigue, improving energy and performance, boosting cortisol in the morning during the wake-up process, possibly also SAD treatment benefits from stimulation of this melanopsin receptor, and/or melatonin suppression. Secondly, the first spectrum is changed into a second spectrum during a second period in time. The second spectrum has a second biological effect which is larger than the first biological effect. Thirdly, the second spectrum is continued during a third period in time. The duration of the second period in time is selected in a range from 5 seconds to 30 minutes.

It has been found that the efficiency of the second spectrum on the biological effect is maximal if the preceding first spectrum changes gradually into the second spectrum in the time period selected in the above-mentioned range. The effect of the preceding first spectrum on the biological effect of the second spectrum is much lower if the transition period is too long. Too short a transition is experienced as unpleasant and therefore undesirable; biologically, such a short transition may be functional. For example, a very short transition period occurs when the first spectrum is generated by a first light source (for example, a lamp or LED), the second spectrum is generated by a second light source, and, as usual, the first light source is switched off at the same time the second light source is switched on to keep the luminance as constant as possible.

It might be that the selected time range is particularly effective because it has a link with the natural habitat of mammals. In nature, spectral variations occur during dawn and dusk with time scales of 1 up to 10 minutes. The internal biological clock of mammals has evolved under these environmental conditions.

The invention can be used to maximize the occurrence of any non-visual, biological effect of light, not only at night but also during daytime.

In an embodiment, the first spectrum has no biological effect. For example, the first spectrum has no blue wavelengths. This allows creating a first period in time wherein the lighting has no biological effect.

In an embodiment, the first spectrum is not switched off during the second period in time, which is also referred to as the transition period. However, its intensity is lower during the second period in time than during the first period in time.

In an embodiment, during the transition period a third spectrum may be present, which may be reduced or absent during the third period in time, to mask the visibility of the transition.

In an embodiment, the light with the first spectrum has a red color and the light with the second spectrum has a blue color. This has the advantage that the light source is relatively simple. In an embodiment, the first spectrum does not have any blue wavelengths at all, while the second spectrum only comprises blue wavelengths.

In an embodiment, the first spectrum is limited to a wavelength in a range from 600 to 760 nm and the second spectrum is limited to a wavelength in a range from 440 to 520 nm. In another embodiment, the first spectrum has a dominant component at a wavelength of 680 nm and the second spectrum has a dominant component at a wavelength of 480 nm. It has been found that the sensitivity of the biological effect to the blue light is raised when the exposure to blue light is preceded by exposure to red light. The sensitivity increase is especially high for the respective wavelengths of 680 nm and 480 nm.

In an embodiment, the first spectrum is white light with a first color temperature, and the second spectrum is white light with a second color temperature which is higher than the first color temperature. By using white light with different color temperatures, the color fidelity is optimal and the transition from the first spectrum to the second spectrum is hardly noticeable.

In an embodiment, the driver repeats the sequence of the first period in time, the second period in time, and the third period in time a predetermined number of times. It appeared that the repetition of the total sequence of the first spectrum, the transition with the specific duration of 10 seconds to 30 minutes, and the second spectrum, maximizes the biological effect.

In an embodiment, after the total sequence of the first spectrum, the transition with the specific duration of 10 seconds to 30 minutes, and the second spectrum, the driver repeats only a sequence of the first spectrum and the second spectrum. The specific transition period in the first sequence seems to improve the efficiency of the further sequences, which do not have the specific transition period of the first sequence.

In an embodiment, during the transition the driver gradually decreases the intensity of the first spectrum and gradually increases the intensity of the second spectrum. This gradual increase and decrease of the respective intensities decreases the visibility of the transition.

In an embodiment, the driver keeps the total luminance or the total brightness of the combined first spectrum and second spectrum constant during the transition period to make the transition even less noticeable.

These and other aspects of the invention are apparent from and will be elucidated with reference to the embodiments described hereinafter.

It should be noted that items which have the same reference numbers in different Figures, have the same structural features and the same functions or are the same signals. If the function and/or structure of such an item has been explained, there is no necessity for repeated explanation thereof in the detailed description.

DETAILED DESCRIPTION OF THE EMBODIMENTS

Figure 1:
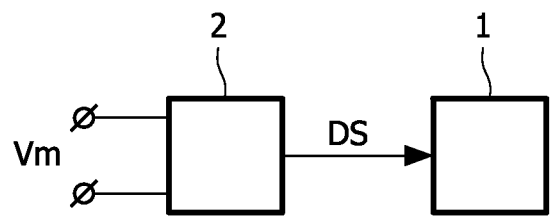
FIG. 1 schematically shows a block diagram of a lighting system.

FIG. 1 schematically shows a block diagram of a lighting system. The lighting system comprises a light source 1 and a driver 2 which drives the light source 1 to emit light with a varying spectrum. The driver 2 receives an input voltage and supplies a current and/or voltage DS to the light source 1. The driver 2 controls the light source 1 to emit successively in time: light with a first spectrum S1, light which changes from the first spectrum S1 into a second spectrum S2, and light with the second spectrum S2. The second spectrum S2 has a biological effect which is larger than the first biological effect. The duration of the transition from the first into the second spectrum is selected in a range from 10 seconds to 30 minutes. This is elucidated in more detail with respect to FIG. 2.

Usually, the driver 2 receives the AC mains voltage Vm and has an electronic circuit for controlling the current through or the voltage across the light source 1. If the light source 1 has different lamps or LEDs, the spectrum of the combined light can easily be varied in a well known manner by changing the ratio of the currents through or voltages across the lamps or LEDs. Usually, LEDs are current driven. Alternatively, also circuits which vary the spectrum of a single lamp, for example by changing the frequency or duty-cycle of the current through, or the voltage across, the single lamp are well known.

The driver 2 may comprise a timer for generating the starting instant and/or setting the durations for the different phases mentioned hereinabove. The driver may comprise an input for receiving a command indicating that a cycle of phases should be started. The command may be a user command.

Figure 2:
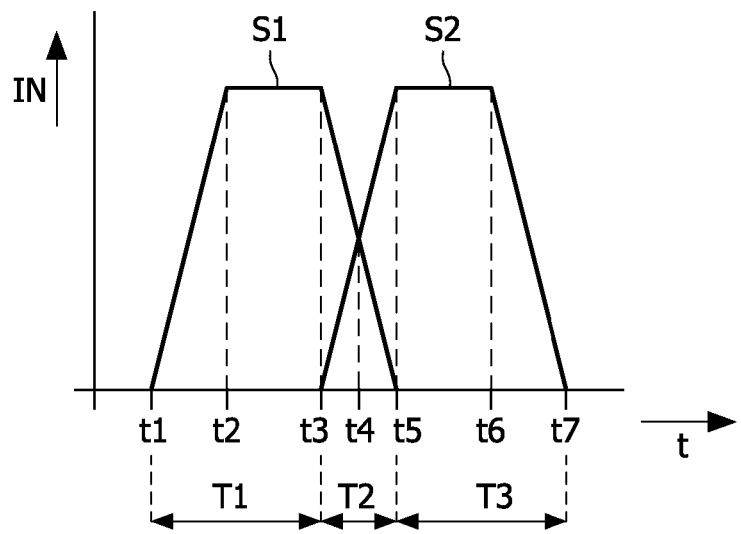
FIG. 2 schematically shows for two spectra a succession in time in accordance with an embodiment of the invention, and FIG. 3 schematically shows a display apparatus.

FIG. 2 schematically shows, for two spectra, a succession in time in accordance with an embodiment of the invention. In the graph, the horizontal axis depicts the time t, and the vertical axis depicts the intensity of the light emitted by the light source 1. At the instant t1, the driver 2 controls the light source 1 to start the emission of light with the first spectrum S1. In the embodiment shown, the intensity gradually increases from zero to a maximum level during the time period lasting from the instant t1 to the instant t2. The first spectrum S1 is generated at full intensity until the instant t3, and decreases gradually to zero at the instant t5. The light source 1 starts emitting the second spectrum S2 with intensity zero at the instant t3. The intensity of the second spectrum S2 gradually increases until a maximum value is reached at the instant t5. The intensity of the second spectrum S2 is kept at its maximum value during the time interval lasting from the instant t5 until the instant t6, and decreases gradually to zero during the time interval lasting from the instant t6 to t7. The second spectrum S2 has a biological effect which is larger than that of the first spectrum S1. The first spectrum S1 may have no biological effect at all.

During the period in time T1, which lasts from the instant t1 to the instant t3, only the first spectrum S1 is emitted. During the period in time T3, which lasts from the instant t5 to t7, only the second spectrum S2 is emitted. During the transition period T2, the first spectrum S1 gradually changes into the second spectrum S2. The transition period T2 is selected to last minimally 10 seconds and maximally 30 minutes. The starting period lasting from the instants t1 to t2 and the switch off period lasting from the instants t6 to t7 may also have a duration selected in a range from 10 seconds to 30 minutes. The exposure duration by the first spectrum S1 and the second spectrum S2 may be selected in the order of minutes.

A lot of alternative embodiments are possible. For example, the light source 1 may be switched on at full intensity at the instant t1, and/or the light source 2 may continue at full intensity until the instant t7 and then be switched off instantly. The maximum intensities of the first spectrum S1 and the second spectrum S2 may differ, for example to obtain the same brightness instead of the same luminance. Although linearly changing intensities are shown, any other gradual or stepwise change of the intensities may be implemented. For example, the changing intensities during the transition period may be sine-wave or Gaussian shaped. The total intensity of the first and the second spectrum may be lower than the maximum value at the instant t4.

The sequence of the spectra S1 and S2 may be repeated a predetermined number of times. In such a repeated sequence, the further sequences may comprise all three phases corresponding to the periods in time T1, T2, T3, or the further sequences may comprise only the two phases corresponding to the periods in time T1 and T3, thus without the transition period T2, or any combination thereof. It is not essential for the present invention that the repeated spectra are identical to the spectra S1 and S2. For example, the first exposure consists of warm (reddish) white light with a very low biological effect and the second exposure consists of cool (bluish) white light which a high biological effect. The duration of the transition between this first and second exposure is selected in the range of 10 seconds to 30 minutes. This complete sub-sequence, which comprises the three phases, may be repeated several times. It is alternatively possible to repeat only the first and second exposures with an in-between transition phase which is shorter than 10 seconds. Alternatively, the repeating sequence may comprise a third exposure which may consist of light with an intermediate color temperature, for example in the range from 4000 to 5000 K, and a fourth exposure which consist of light which is identical to the light emitted during the second exposure.

Finally, in an embodiment, the present invention uses a special first light exposure with a first spectrum to maximize the non-visual effect of the succeeding second light exposure with a second spectrum, which has a higher non-visual effect than the first spectrum. For example, the first spectrum is red-rich light and the second spectrum is blue-rich light. Further, the transition period, in which the first spectrum is changed into the second spectrum, has a duration selected in the range from 10 seconds to 30 minutes. Such a duration of the transition period maximizes the non-visual, biological effect on the illuminated mammal. For example, the non-visual biological effect is: phase shifting of a wake/sleep rhythm, inducing alertness, reducing sleep or fatigue, improving energy and performance. In an embodiment, the transition is performed such that it is minimally visible to the observer.

The first spectrum may consist of light which predominantly contains energy within the long wavelength range, for example warm white light with a color temperature in the range from 2700 to 4000 K. The second spectrum may consist of light which predominantly contains energy within the short wavelength range, for example cool white light with a color temperature in the range from 5000 to 17000 K.

Figure 3:
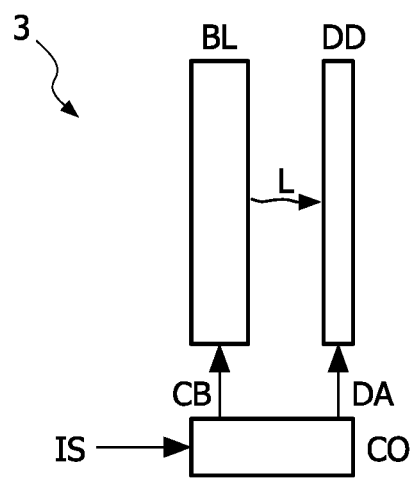

FIG. 3 schematically shows a display apparatus. The display apparatus 3 comprises the backlight unit BL, a pixilated display device DD, and a controller CO. The controller CO receives the input signal IS, which represents an image, and supplies data and control signals DA to the display device DD, and a control signal CB to the backlight unit BL. The image may be a natural scene (photo, video) or may be computer generated. The control signal CB controls the spectrum of the light source(s) 1 in the backlight unit BL. The controller CO may comprise a timer to control the timing of the different phases of the sequence of the different spectra S1 and S2. The backlight unit BL may comprise the driver 2 (see FIG. 1), which provides the current/voltage to the light source(s) 1 to obtain the light L for illuminating the display device DD. For example, the display device DD is an LCD or DMD. For example, the back light unit may comprise fluorescent tube(s) and/or LEDs.

The present invention may be implemented in several applications, such as for example:
office lighting, for example to improve early morning activity and to reduce after-lunch fatigue,
hospital lighting, for example to reduce sleep inertia of medical staff upon nocturnal wake-up,
care home lighting, for example to reduce day-time napping of elderly to improve nocturnal sleep duration and sleep quality,
control rooms, for example to obtain sustained alertness during 24 hours operation and night shift work, and
automotive lighting, for example alternating in-car exposure to low intensity red and blue LEDs to improve driver alertness.

It should be noted that the above-mentioned embodiments illustrate rather than limit the invention, and that those skilled in the art will be able to design many alternative embodiments without departing from the scope of the appended claims.

For example, the light sources may comprise a full spectrum light emitting device and (switchable) filters to generate the different spectra. Such filters may comprise electrochrome, electrophoretic, liquid crystal cells comprising (dichroic) dyes or based on electrowetting.

The present invention may be combined with existing dynamic lighting systems. For example, a sequence of sub-sequences is added in the morning to further improve the alertness of the subject. The first sub-sequence of this sequence has the three phases, while the successive sub-sequences have three or two phases. Such existing dynamic lighting systems vary the color temperature and intensity of a light source over the day. However, these prior art lighting systems do not provide the sequences of the three phases, and change the color temperature of the emitted light very slowly during transition periods of one hour or more.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A lighting system for creating a biological effect induced by light, the biological effect being a different effect than vision, and the lighting system comprising:
    at least one light source for generating light with a varying spectrum, and
    at least one driver for driving the lighting system to, successively in time:
        generate a first spectrum (S1) during a first period in time (T1),
        change the first spectrum (S1) into a second spectrum (S2) during a second period in time (T2), the second spectrum (S2) having the biological effect, and
        continue the second spectrum (S2) during a third period in time (T3), wherein a duration of the second period in time (T2) is selected in a range from 5 seconds to 30 minutes;
    said light of said first spectrum having a red color and said light of said second spectrum having a blue color;
    said first spectrum being a wavelength of about 600 nm to about 760 nm and said second spectrum being a wavelength of about 440 nm to about 520 nm.

2. A lighting system as claimed in claim 1, further comprising a third spectrum selected for masking a transition from the first spectrum (S1) into the second spectrum (S2) during at least part of the second period in time (T2).

3. A lighting system as claimed in claim 1, wherein the first spectrum (S1) has a dominant component at a wavelength of 680 nm and the second spectrum (S2) has a dominant component at a wavelength of 480 nm.

4. A lighting system as claimed in claim 1, wherein the driver (2) is constructed for further repeating the sequence of the first period in time (T1), the second period in time (T2), and the third period in time (T3) a predetermined number of times.

5. A lighting system as claimed in claim 1, wherein the driver (2) is constructed for further repeating the sequence of the first period in time (T1) and the third period in time (T3).

6. A lighting system as claimed in claim 1, wherein the driver (2) is constructed for gradually decreasing an intensity (IN) of the first spectrum (S1) and gradually increasing an intensity (IN) of the second spectrum (S2).

7. A lighting system as claimed in claim 6, wherein the driver (2) is constructed for keeping a total luminance or a total brightness of the first spectrum (S1) and the second spectrum (S2) constant during the second period in time (T2).

8. A method of driving a light source (1), the method comprising successively the steps of:
   generating a first spectrum (S1) during a first period in time (T1),
   changing the first spectrum (S1) into a second spectrum (S2) during a second period in time (T2), the second spectrum (S2) having a biological effect induced by light generated by the light source, the biological effect being a different effect than vision, and
   continuing the second spectrum (S2) during a third period in time (T3), wherein a duration of the second period in time (T2) is selected in a range from 5 seconds to 30 minutes;
   said light generated in said first spectrum having a red color and said light generated in said second spectrum having a blue color;
   limiting said first spectrum light to a wavelength in a range of about 600 nm to about 760 nm;
   limiting said second spectrum light to a wavelength in a range of about 440 nm to about 520 nm.

9. A method of driving a light source, the method comprising:
   gradually increasing light output from a first light source to a defined output of a first spectrum during a first period in time to substantially emit said light of said first spectrum;
   gradually decreasing said light output from said first light source during a second period of time;
   during said second period of time, gradually increasing light output from a second light source having a second spectrum to a defined light output of said second light source;
   wherein said first spectrum is a red color and said light output of said first light source is maintained between a wavelength of about 600 nm to about 760 nm and said second spectrum is a blue color and said light output of said second light source is maintained between a wavelength of about 440 nm to about 520 nm;
   during a third period of time, maintaining said light output from said second light source at said second spectrum while maintaining said light output of said first light source to near zero to substantially emit said blue color;
   said second spectrum having a biological effect induced by light generated by said second light source, said biological effect being a different effect than vision; and
   continuing said second spectrum during said third period in time, wherein a duration of the second period in time is selected in a range of from about 5 seconds to about 30 minutes.

* * * * *